United States Patent [19]

Cosmai

[11] Patent Number: 4,856,567

[45] Date of Patent: Aug. 15, 1989

[54] LOADER-MIXER DEVICE FOR ENDERMIC INJECTORS

[75] Inventor: Pietro Cosmai, Gorizia, Italy

[73] Assignee: Sicim SpA, Romans D'Isonzo, Italy

[21] Appl. No.: 76,362

[22] Filed: Jul. 22, 1987

[30] Foreign Application Priority Data

Aug. 4, 1986 [IT] Italy ................... 83390 A/86

[51] Int. Cl.$^4$ ................... B65B 3/02; A61M 5/30
[52] U.S. Cl. ................... 141/302; 141/21; 141/104; 141/309; 141/330; 604/70; 604/405; 604/411
[58] Field of Search ................... 141/21-29, 141/104, 301-310, 285, 319, 329, 330, 242, 243; 604/403, 405, 411-415, 70, 71, 82-92

[56] References Cited

U.S. PATENT DOCUMENTS

| | | | |
|---|---|---|---|
| 1,321,198 | 11/1919 | Ferguson et al. | 141/25 |
| 2,737,946 | 3/1956 | Hein Jr. | 604/70 |
| 2,928,390 | 3/1960 | Venditty et al. | 604/70 |
| 3,330,276 | 7/1967 | Gordon | 604/71 |
| 3,330,277 | 7/1967 | Gabriels | 604/71 |
| 3,526,225 | 9/1970 | Isobe | 604/71 |
| 3,714,943 | 2/1973 | Yamef et al. | 604/70 |
| 3,827,601 | 8/1974 | Magrath et al. | 222/83 |
| 3,874,381 | 4/1975 | Baum | 141/27 X |
| 3,908,651 | 9/1975 | Fudge | 604/71 |
| 3,949,746 | 4/1976 | Walloch | 141/243 X |
| 4,171,710 | 10/1979 | Boynton et al. | 141/104 X |
| 4,253,501 | 3/1981 | Ogle | 141/27 |
| 4,470,431 | 9/1984 | Shackelford et al. | 141/104 X |
| 4,507,113 | 3/1985 | Dunlop | 604/411 |
| 4,532,969 | 8/1985 | Kwaan | 141/27 |
| 4,534,758 | 8/1984 | Akers et al. | 604/85 |
| 4,623,332 | 11/1986 | Lindmayer et al. | 604/68 |
| 4,626,242 | 12/1986 | Fejes et al. | 604/68 |
| 4,642,095 | 2/1987 | Dettbarn et al. | 604/72 |
| 4,684,365 | 8/1987 | Reinicke | 604/413 X |

FOREIGN PATENT DOCUMENTS 0114792 1/1984 European Pat. Off. .

Primary Examiner—Ernest G. Cusick
Attorney, Agent, or Firm—Flynn, Thiel, Boutell, & Tanis

[57] ABSTRACT

Loader-mixer device for endermic injectors which is suitable to cooperate with a portable endermic injector momentarily in loading, by aspiration through an injection-aspiration nozzle included in an injection head (17) of the portable endermic injector, the product to be injected, the device comprising in cooperation:
  at least one seating to lodge and position phials (12) together with two needles (13-14),
  a socket (31) to position the injection head (17), and
  a selector assembly (20) to connect a phial (12) to the injection head (17) as required.

7 Claims, 2 Drawing Sheets

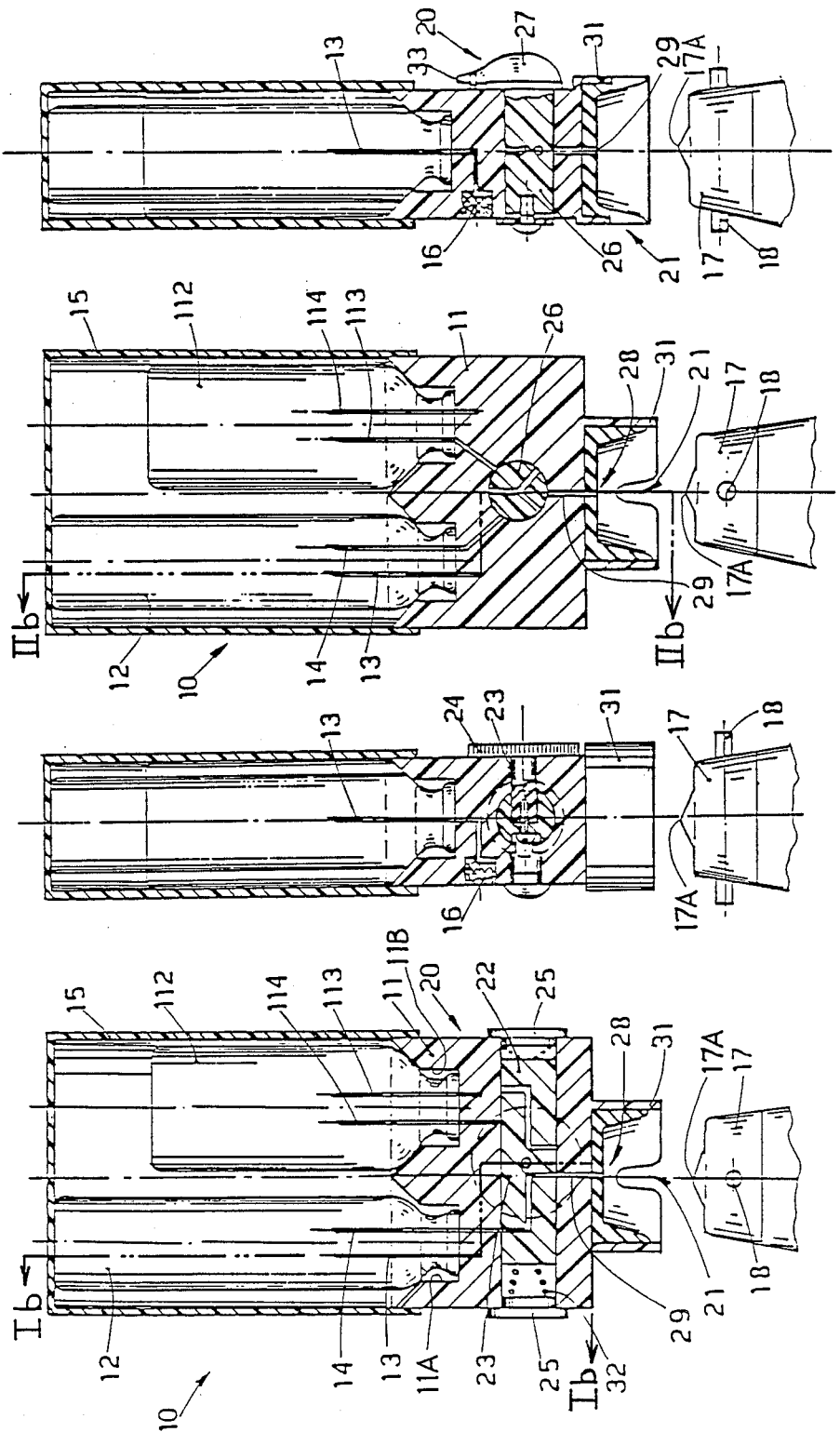

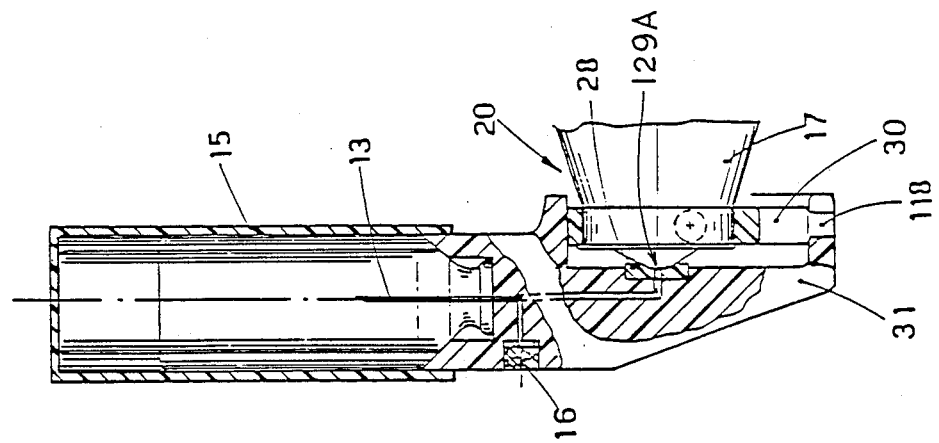
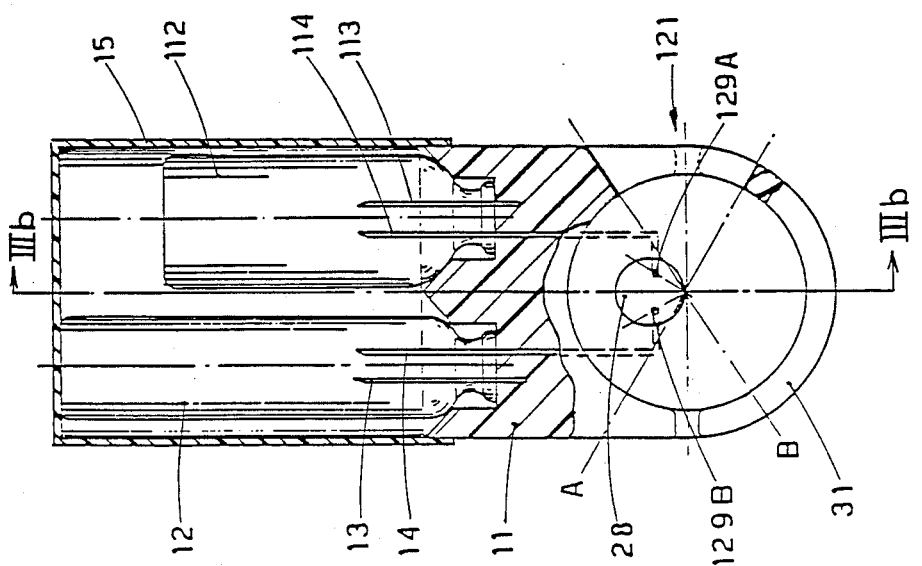

LOADER-MIXER DEVICE FOR ENDERMIC INJECTORS

FIELD OF THE INVENTION

This invention concerns a loader-mixer device for portable endermic injectors of a type not including a phial holder.

The invention therefore concerns a loader-mixer device which is suitable to be fitted or coupled momentarily to a portable endermic injector so as to enable the injector to aspirate a medicinal substance directly from appropriate phials.

To be more exact, the invention concerns a loader-mixer device able to hold at least one but advantageously two phials containing a product which can be loaded, perhaps with the mixing of the two components, by aspiration by the endermic injector directly through its injection and aspiration nozzle.

DESCRIPTION OF THE RELATED ART

Portable endermic injectors of a mechanical type are known which comprise an aspiration and containment chamber, an aspiration and energy-storage assembly, a cocking and ejection assembly and an assembly to read the quantity aspirated, in which those injectors have:

a containment assembly, which includes the aspiration and containment chamber and a plunger, is screwed to a frontal container, the aspiration and energy-storage assembly comprises means to regulate the pre-loading of a spring assembly, such means consisting of spacer rings and of elements which can be positioned axially and reciprocally in a variable manner, and the reader assembly comprises a threaded area and a slider which cooperates with a graduated scale,
the injection head being equipped with means for its anchorage to and/or positioning in relation to loader-mixer devices.

The present applicant has no knowledge of any existing loader-mixer devices of the type which is the subject of this invention.

SUMMARY OF THE INVENTION

According to the invention a support is provided to bear, hold and position at least one and advantageously two phials. This support comprises two pairs of needles, which cooperate with appropriate phials holding medicinal substances and capable of being fitted within the support.

Of such pairs of needles, one needle of each pair performs aeration and communicates with the exterior through a filter, whereas the other needle of each pair is suitable to feed the portable endermic injector momentarily in cooperation with the corresponding needle of the other pair.

The two feeder needles cooperate with the injection head of the injector in feeding the substances held in the phials to the injector.

A selector assembly is included in cooperation with the outlets of the needles and with the injection head and is able to put first one outlet, then the other outlet in communication with the injection head so that the required liquid can be aspirated in the desired quantity from one phial and/or the other.

The invention is therefore embodied with a loader-mixer device for endermic injectors which is suitable to cooperate with a portable endermic injector momentarily in loading, by means of aspiration through an injection-aspiration nozzle included in an injection head of the portable endermic injector, the product to be injected, the device being characterized in that it comprises in cooperation:

at least one seating to lodge and position phials together with two needles, a socket to position the injection head, and a selector assembly to connect a phial to the injection head as required.

BRIEF DESCRIPTION OF THE DRAWINGS

The attached figures, which are given as a non-restrictive example, show the following:

FIG. 1a is a central cross-sectional view of a loader-mixer device with a slide valve selector assembly;

FIG. 1b is a sectional view substantially as taken on the line Ib—Ib of FIG. 1a;

FIG. 2a is a central cross-sectional view of a modified loader-mixer device with a selector assembly comprising a rotary distributory shaft;

FIG. 2b is a sectional view substantially as taken on the line IIb—IIb of FIG. 2a;

FIG. 3a is an elevational view, partly broken away in central cross-section, of a further modified loader-mixer device with a selector assembly acting on the injection head;

FIG. 3b is a side elevational view partly broken away in cross-section, generally along the line III—IIIb of FIG. 3a.

DESCRIPTION OF THE PREFERRED EMBODIMENT(S)

In the figures the same parts or parts having the same functions bear the same reference numbers.

Two positioner seatings 11a–11b for standard phials 12-112 are provided in a support 11 and may also be pre-arranged for special phials or be adaptable for special phials.

Two pairs of needles 13-14-113-114 protrude from each support 11 and perform the functions of aeration (aerator needles 13-113) and delivery (delivery needles 14-114) respectively. These pairs of needles 13-14, with the phials 12 installed, cooperate with the inside of the phials.

When installed in the support 11, the phials 12-112 can be protected by fitting an appropriate cover 15.

The aerator needles 13-113 communicate with the outside environment through a filter 16, which serves to prevent contamination. The filter can be replaced and be made of a material suitable to prevent the breeding of germs and also able to kill them.

The delivery needles 14-114 cooperate with a delivery selector assembly 20, which provides the delivery and the type of product to be delivered to an injection head 17 during the aspiration step of that head.

The injection head 17 is fitted in an appropriate socket 31 and is positioned with the help of rods 18 cooperating either with an alignment notch 21 or a positioning notch 121.

An appropriate support seating 28, which consists advantageously of a resilient material, is provided in cooperation with the area about an aspiration and injection nozzle 17a in the injection head 17. A delivery nozzle 29 is included in the support seating 28 and cooperates with the aspiration and injection nozzle 17a of the injection head 17.

The delivery nozzle 29 is put in communication by the selector assembly 20 with one phial 12 or with the other phial 112 or does not communicate with either phial 12-112.

The embodiment of FIG. 3 provides for two delivery nozzles 129A and 129B, one for each phial 12-112.

The alignment notch 21 serves to position the injection head 17 in such a way that the aspiration and injection nozzle 17a of that head is aligned as accurately as possible with the delivery nozzle 29.

The positioner notch 121 of FIG. 3 serves to determine two angular positions A and B of the injection head 17 within the socket 31 of FIG. 3.

The embodiment of FIG. 3 provides for the aspiration and injection nozzle of the injection head 17 to be eccentric in relation to the axis of the socket 31 and to the axis of angular rotation of the endermic injector. Such eccentric positioning can be machined directly in the injection head 17 or be obtained with an eccentric ring 30 fitted for this purpose to the injection head 17 and also comprising rods 118.

In a variant the eccentric ring 30 can rotate in the socket 31 but cannot be extracted, and the injection head 17 is inserted momentarily into that ring 30, creating therewith the required torsional anchorage, for instance by means of the rods 18 included in the injection head 17.

In the embodiment of FIG. 3, if the injection head 17 is rotated with its axis at A, the injection and aspiration nozzle of the injection head is put in communication with the delivery nozzle 129A owing to the eccentric positioning.

If the injection head 17 is rotated with its axis at B, the injection and aspiration nozzle is put in communication with the delivery nozzle 129B. When not in positions at A or B, the selector assembly does not provide communication or loading.

In the embodiment of FIG. 3 the complex consisting of the delivery nozzles 129, eccentric ring 30 and positioner notches 121 which make possible the positions A and B, constitutes the selector assembly 20.

In FIG. 1 the selector assembly 20 consists of a slide valve 22 with suitable ducts able to put the delivery nozzle 29 in communication first with the delivery needle 14 and then with the delivery needle 114.

Axial displacement of the slide view 22 can be obtained with the help of a knob 24 that cooperates with a slot 23 which limits and determines such displacement, so that at the end of the displacement in the slot the communications between the delivery needles 14-114 and the delivery nozzle 29 are defined.

Springs 32 may be included to return the slide valve 22 to a central position where the needles 14-114 and delivery nozzle 29 are not in communication with each other when delivery to the injection head 17 is not required.

Plugs 25 may be provided for lateral closures.

In FIG. 2 the selector assembly 20 consists of a distributor shaft 26 able to rotate by a given angle about its own axis, a duct shaped like an overturned "Y" being located within such shaft. This given angle serves to put (FIG. 2a) the needles 14-114 respectively in communication with the delivery nozzle 29.

Such given angle can be provided by positioners 33 cooperating with a pointer 27 solidly fixed to the shaft 26.

Springs may be included to return the shaft 26 to a neutral position as shown in FIG. 2a.

All the parts are fitted in such a way that they can be readily dismantled for the cleaning of the various parts.

A suitable plug is provided to close the socket 31 when it is not necessary to deliver medicament to the injection head 17.

Various materials may be employed such as plastics, stainless steel, aluminium, etc.

I claim:

1. Loader-mixer device for endermic injectors which is suitable to cooperate with a portable endermic injector momentarily in loading, by means of aspiration through an injection-aspiration nozzle included in an injection head of the portable endermic injector, the product to be injected, the loader-mixer device comprising:
   at least one seating to lodge and position a respective phial together with two needles,
   a socket to position the injection head, and
   a selector assembly to connect one of the two needles to the injection head, in which the selector assembly comprises at least one delivery nozzle positioned eccentrically in said socket for cooperating with at least one angular limit position (A-B) of an injection head to be inserted in said socket, namely an injection head of a kind having an injection-aspiration nozzle which is not aligned with a central longitudinal axis of angular rotation of the endermic injector.

2. Device as claimed in claim 1, in which the two needles comprise an aeration needle, and a delivery needle.

3. Device as claimed in claim 2, including a filter interposed between the outside environment and the aeration needle.

4. Device as claimed in claim 1, wherein said at least one seating includes a plurality of seatings to lodge and position respective phials, in which the selector assembly has a specific loading position for each phial.

5. Device as claimed in claim 1, in which the selector assembly has a position in which it does not provide communication or loading.

6. Apparatus for loading an endermic injector, such apparatus comprising, in combination:
   an endermic injector of the kind having an injection head and an axis of angular rotation including an injection-aspiration nozzle;
   a loader-mixer device for said endermic injector, said loader-mixer device including:
   (a) at least one seating to lodge and position a respective phial, and two needles projecting into said at least one seating to communicate with a phial therein,
   (b) a socket to receive and position the injection head, said socket and injection head having cooperating means permitting angular rotation of said injection head between angular limit positions (A-B) in said socket, the injection-aspiration nozzle being eccentric in relation to an axis of the socket and to said axis of angular rotation of said injection head of the endermic injector, and
   (c) a selector assembly to connect one of the two needles to the injection head, in which the selector assembly comprises at least one delivery nozzle cooperating with at least one angular limit position (A-B) of the injection head, in which position said at least one delivery nozzle is not aligned with said axis of angular rotation of the endermic injector but is aligned with said injector-aspiration nozzle of said endermic injector.

7. Loader-mixer device for endermic injectors which is suitable to cooperate with a portable endermic injector momentarily in loading, by means of aspiration through an injection-aspiration nozzle included in an injection head of the portable endermic injector, the product to be injected, the loader-mixer device comprising:

at least one seating to lodge and position a respective phial together with two needles, a socket to position the injection head, and a selector assembly to connect one of the two needles to the injection head, in which the selector assembly comprises at least one delivery nozzle positioned eccentrically in said socket for cooperating with at least one angular limit position (A-B) of an injection head to be inserted in said socket, namely an injection head of a kind having an injection-aspiration nozzle which is not aligned with a central longitudinal axis of angular rotation of the endermic injector, said selector member comprising a disklike member seated eccentrically in said socket and having a pair of said delivery nozzles therein connected to respective ones of said needles, and means on said socket for allowing limited rotational movement of the injection head in said socket.

* * * * *